(12) United States Patent
Puhasm•gi et al.

(10) Patent No.: US 9,233,230 B2
(45) Date of Patent: Jan. 12, 2016

(54) CATHETER INTRODUCER ASSEMBLY

(75) Inventors: Arne Puhasm•gi, Borås (SE); Anne Lundgren, V•stra Fr•lunda (SE)

(73) Assignee: NORDIC MED-COM AB, Bor?s (SE)

( * ) Notice: Subject to any disclaimer, the term of this patent is extended or adjusted under 35 U.S.C. 154(b) by 0 days.

(21) Appl. No.: 14/241,089

(22) PCT Filed: Sep. 5, 2012

(86) PCT No.: PCT/SE2012/050940
§ 371 (c)(1),
(2), (4) Date: Feb. 26, 2014

(87) PCT Pub. No.: WO2013/036193
PCT Pub. Date: Mar. 14, 2013

(65) Prior Publication Data
US 2014/0221932 A1     Aug. 7, 2014

(30) Foreign Application Priority Data
Sep. 9, 2011   (SE) ...................................... 1150815

(51) Int. Cl.
*A61M 25/06*     (2006.01)
*A61M 25/00*     (2006.01)
(Continued)

(52) U.S. Cl.
CPC ......... *A61M 25/0606* (2013.01); *A61M 1/3661* (2014.02); *A61M 25/0097* (2013.01); *A61M 39/227* (2013.01); *A61M 2039/0666* (2013.01); *A61M 2039/229* (2013.01)

(58) Field of Classification Search
CPC .................. A61B 17/3498; A61M 2039/0673; A61M 2039/062; A61M 39/0208; A61M 1/3653; A61M 2039/027; A61M 2039/0633; A61M 2039/0666; A61M 39/06; A61M 25/0097; A61M 1/3661; A61M 25/0606
USPC ........ 604/29, 43, 44, 164.01, 167.01, 167.03, 604/167.06
See application file for complete search history.

(56) References Cited

U.S. PATENT DOCUMENTS

| 4,324,236 A | 4/1982 | Gordon |
| 4,960,412 A | 10/1990 | Fink |

(Continued)

FOREIGN PATENT DOCUMENTS

| DE | 19619065 | 11/1997 |
| EP | 0568258 | 11/1993 |

(Continued)

OTHER PUBLICATIONS

Written Opinion issued in PCT/SE2012/050940, Aug. 1, 2013, pp. 1-6.

(Continued)

*Primary Examiner* — Laura Bouchelle
(74) *Attorney, Agent, or Firm* — Jeffrey S. Melcher; Manelli Selter PLLC

(57) ABSTRACT

The present invention relates to a valve assembly for sealing a through passage of a catheter introducing device, comprising a sealing unit having a movable closing member connected to a biasing means, and a seat member arranged with a sealing surface around the aperture of the through passage, wherein the biasing means is arranged to urge the closing member to sealably abut against the sealing surface, corresponding to a closed position, so as to prevent flow of fluid through the valve. The invention also relates to a catheter introducer assembly comprising a valve assembly.

5 Claims, 11 Drawing Sheets

(51) Int. Cl.
*A61M 1/36* (2006.01)
*A61M 39/22* (2006.01)
*A61M 39/06* (2006.01)

(56) References Cited

U.S. PATENT DOCUMENTS

| | | | |
|---|---|---|---|
| 5,290,245 A * | 3/1994 | Dennis | 604/167.03 |
| 5,403,284 A * | 4/1995 | Gross | 604/167.03 |
| 5,755,702 A * | 5/1998 | Hillstead et al. | 604/264 |
| 5,827,228 A | 10/1998 | Rowe | |
| 6,692,467 B2 * | 2/2004 | McFarlane | 604/167.03 |
| 2003/0167040 A1 | 9/2003 | Bacher | |
| 2007/0265571 A1* | 11/2007 | Utterberg et al. | 604/174 |
| 2008/0097386 A1 | 4/2008 | Osypka | |

FOREIGN PATENT DOCUMENTS

| | | |
|---|---|---|
| EP | 1418963 | 5/2004 |
| JP | S60-146972 | 2/1985 |
| JP | S60146972 | 8/1985 |
| JP | S63-151152 | 10/1988 |
| JP | S63-151152 U | 7/2002 |
| JP | 2003-325671 | 11/2003 |
| JP | 2004-509660 | 4/2004 |
| JP | S40-025973 | 9/2004 |
| JP | 2009-530057 | 8/2009 |
| WO | 2008/068720 | 6/2008 |
| WO | 2008068720 A2 | 6/2008 |
| WO | 2010/132608 | 11/2010 |

OTHER PUBLICATIONS

International Search Report issued in PCT/SE2012/050940, Aug. 1, 2013, pp. 1-4.
European Office Action issued in European Patent Application No. 12829552.4, Mar. 30, 2015, pp. 1-9.
Office Action issued in Korean Patent Application No. 2014-700931, Sep. 22, 2014, pp. 1-4.
Office Action issued in Japanese Patent Application No. 2014-529641, Sep. 30, 2014, pp. 1-12.
Japanese Office Action issued in Japanese Patent Application No. 2014-529641, Jul. 2, 2015, pp. 1-2, translation included.

* cited by examiner

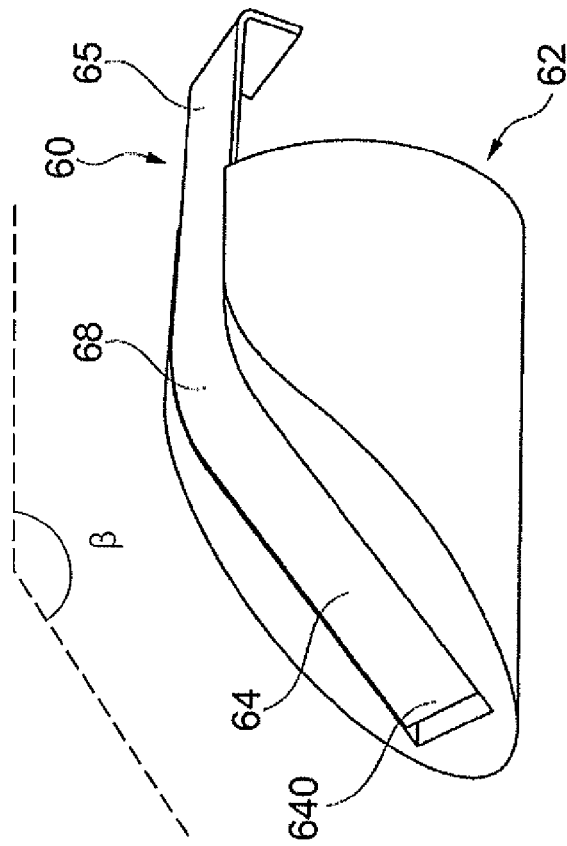
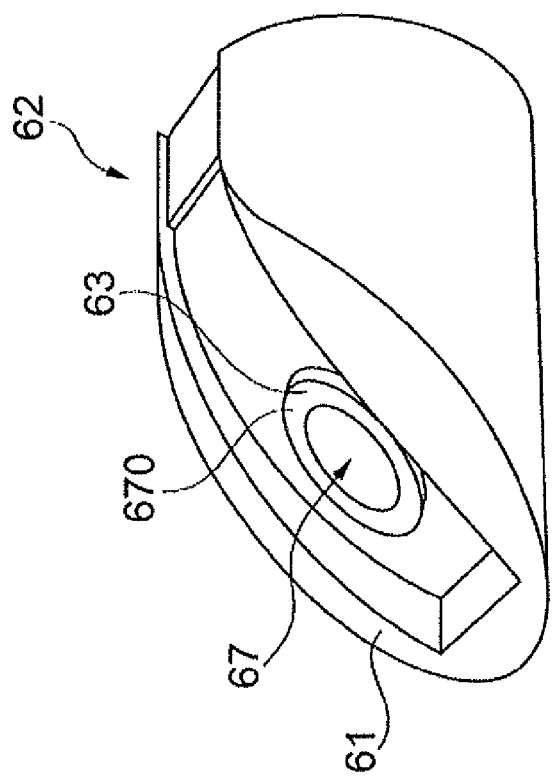
Fig. 6C
Fig. 6B

CATHETER INTRODUCER ASSEMBLY

TECHNICAL FIELD

The present invention relates to a device for conveying fluid media into or out of the body of a patient in a subcutaneous, intravascular or intramuscular way.

BACKGROUND OF THE INVENTION

Many medical situations and treatments are associated with the need for conveying fluid media into or out of the body of a patient. Access to a person's circulatory system, such as the cardiovascular or the cerebrospinal fluid system, is often achieved by means of introducing a catheter tube into the patient in a subcutaneous, intravascular or intramuscular way. Insertion of a catheter is done by means of a needle element, wherein the needle point is used for punctuating e.g. a vein and subsequently introducing the catheter before withdrawing the needle, leaving only the soft catheter tube which for instance may be connected to a source of fluid to be administered into or from the vein.

A typical example of such medical situation is blood dialysis (usually hemo-dialysis), which sometimes is required as a consequence of kidney malfunction. In dialysis, two catheter tubes are inserted into a so called fistula which is created by connecting an artery to a vein. One catheter is used for withdrawal of blood and the other for reinserting it into the patient. Dialysis treatment is a rather delicate and exposed situation for the patient and it is desired to provide a very cautious and careful handling during the penetration of the patient's skin or fistula wall or during the continued treatment.

A common problem related to dialysis treatment (as well as to any situation involving insertion procedure for a catheter tube) is the risk of blood leakage, particularly when connecting the dialysis equipment to the fistula. Typically, the needle used for connecting the assembly to a fistula has quite a large diameter (often larger than 1.6 mm) in order to provide for sufficient volume of blood passage during the time dialysis is run, and at the same time avoiding rupture of the blood cells which are passing at a high flow rate. The large needle in combination with the high pressure in a fistula leads to the risk that blood from the circulation system often escapes, either when connecting the catheter to the fistula or during treatment, resulting in a leakage of blood which is of course highly undesired as it makes an already uneasy and exposed situation even worse for the patient, and also leads to a risk for blood contamination for health care providers.

As the blood pressure within a fistula is very high, penetration will lead to a heavy and immediate outflow of blood. This naturally puts extremely high demands on the equipment/catheter assemblies which are intended to be used for transferring the blood from the patient to the dialysis equipment and again back to the patient. A catheter assembly used in dialysis should be designed to handle over—as well as sub-pressure since each fistula is connected to two catheters: one for the withdrawal of blood and one for reintroducing it into the patient. The assembly through which blood will be withdrawn will be subjected to a subpressure and the assembly through which blood is to be transferred back to the patient will be subjected to a overpressure. In each of those situations there is a risks that the pressure difference inside the catheter hub compared to the ambient pressure leads to failure of the assembly components with leakage as consequence.

Another risk associated with extracorporal treatment is the occurrence of turbulence in the blood flow leading to risk of damage to the blood cells (hemolysis) which, as a result of the frequently reoccurring treatments that the patient is subjected to, gradually would degenerate the patient blood and in the long run represent a serious health risk.

Another problem which may pose a serious problem during a dialysis treatment is the risk of clotted/coagulated blood which sometimes is formed inside the catheter introducer assembly running the risk of entering into the dialysis equipment and/or into the patients. A blood clot unintentionally entering a blood circulation system of a patient could lead to serious health risks and even be fatal.

In one type of catheter assembly, the fistula is penetrated by a needle which is subsequently withdrawn only leaving the catheter tube for transferral of blood or liquid. This is advantageous since a soft catheter tube will not run the risk of damaging the patient's fistula/skin the way a dialysis needle could. However, retracting the cannula (often a metal needle) out of the instrument sometimes gives rise to undesired friction drag between the needle and the assembly wherefrom it is to be removed, which in its turn may lead to an inert or even irregular retraction motion which is of course a disadvantage: preferably connection of a catheter tube should be performed smoothly and without sudden interruptions.

Many examples of sealing devices for assemblies exist, aiming to prevent leakage in various forms, e.g. leakage of blood. For instance in U.S. Pat. No. 4,960,412, there is seen a catheter introducing system with a so called "duckbill"-solution, and in U.S. Pat. No. 5,403,284 there is described an automatic shut-off mechanism for a catheter tube assembly. However due to the specific circumstances related to certain treatments such as dialysis, according to our knowledge, no prior art arrangement has yet presented a fully satisfactory solution for connecting to a catheter assembly. Existing catheter introducing assemblies are often quite complicated to handle, and may e.g. require at least two hands during the introducing procedure which makes the connection of the catheter laborious for the professional health care provider as well as it eliminates the possibility of self-treatment at home: the operation is simply too difficult to perform by oneself.

OBJECTS OF THE INVENTION

It is an object of the present invention to provide an arrangement which provides at least one of the following advantages:—an improved and user-friendly catheter introducer system, a safe and robust valve/sealing arrangement for a catheter introducing assembly, —a safe media transfer system with minimised risk for leakage,—a smooth media transfer through the assembly with low risk of turbulence and (for instance) blood cell rupture,—a robust and reliable construction which at the same time allows for easy withdrawal of a needle element subsequent to connecting of the catheter to the fistula, and—which eliminates the risk of accidental entering of clotted blood into the blood circulation system and/or the dialysis equipment.

DESCRIPTION OF THE INVENTION

The object/s of the invention is achieved substantially by means of a valve assembly and a catheter introducer assembly according to the claims.

Thanks to the invention there is provided a catheter introducer assembly which provides for a safe and smooth connection of a catheter tube to a patient where the valve assembly, immediately upon retraction of the needle, will form a secure and tight seal so that leakage of any media (such as blood) is minimized or prevented, even for high blood pressures as in dialysis treatments. Upon removal of the needle from the assembly a valve biasing means will urge the valve to assume a sealed configuration/position so as to prevent accidental leakage of fluid/media from the assembly.

Another advantage is that the catheter introducer assembly, as well as the valve assembly according to the invention, comprises few parts, which contributes to that it is uncomplicated to assemble. Also, mounting together of an assembly is possible while keeping the sensitive sharp point of the needle untouched which ensures that it is not damaged when piercing e.g. a fistula: a damaged needle point could easily rupture the fistula and cause unnecessary harm to it.

For ease of description, the ends of the components of the device described herein are referred to as "frontal" and "rear", i.e., the frontal end referring to the end which encounters the body first upon insertion of a catheter into a patient or which is closest to the body of the patient during use. The term "proximal" when used in reference to a needle, hub, or catheter, refers to the frontal end thereof which is inserted into the patient's body. The term "distal" when used in reference to a needle, hub, or catheter, refers to the rearward end thereof which is situated externally of the patient's body and closest to a user (such as a health care provider) of the device.

The design of the assembly, and in particular of the valve assembly, gives rise to a minimised friction drag between the needle surface and the seal enabling a smooth and continuous retraction of the needle out from the assembly hub without any unexpected and/or sudden motions.

An assembly according to the present invention provides a reliable, easy to use connector with a self-sealing valve preventing blood leakage both upon connecting the catheter to a patient and during ongoing treatment, such as while performing dialysis treatment.

According to one embodiment of the invention, the assembly comprises a bifurcated housing having two converging conduits, whereof one conduit is connected between the catheter and a distal conduit. The distal conduit may, in its turn, for instance be coupled to a dialysis equipment. In such embodiment, in addition to providing an extremely reliable seal, the valve assembly is preferably designed so that the valve components upon assuming a closed configuration will create an inner wall of a conveying chamber which is created as a result of closure of the valve, and which serves as a passage between the catheter and the distal conduit. When said valve has assumed a closed position the conveying chamber will have a cross section essentially void of any abrupt changes, which is very beneficial in order to promote an even flow path for passing blood or liquid between the catheter and the distal conduit. An even blood flow will reduce the risk of turbulence during transfer of blood through the hub and minimize the risk of hemolysis, which could be the case if uneven flow would cause rupture of the blood cells.

It is to be understood that the assembly described herein may be used in various situations involving the conveying of blood or other liquid to/from a patient, such as for instance dialysis treatment, intravenous therapy or other medical treatments. For the sake of convenience, in the following description the liquid to be transferred is often referred to as "blood", however it is to be understood that also other liquids, fluids or media are to be included in this term, e.g. dialysis liquid or intravenous liquid. This further means that the device according to the invention, and in particular the sealing valve assembly according to the invention, is suitable for situations involving/assemblies used when administering media into or out of a patient's body in a subcutaneous, intravascular and/or intramuscular way, where prevention of leakage (e.g. leakage of blood, cerebrospinal fluid, intravenous medical fluids, intravenous hyperalimentation, amongst others) is desired.

A sealing device according to the invention provides for a catheter assembly where the friction drag between the valve and the cannula at withdrawal of the cannula is minimised, with a self sealing valve preventing (blood) leakage immediately when the cannula is retracted, which is non-reusable, which can be sterilized and which in its closed configuration will resist overpressure as well as subpressure.

According to one aspect of the invention said valve assembly comprises a straight through passage, arranged to be aligned with said rear passageway of the hub, wherein the valve assembly in said open position will allow for said cannula to extend through said straight through passage, and wherein the valve assembly in said closed position will seal the rear passageway of the hub thus preventing passage of blood or dialysis liquid through said rear passageway as well as preventing forward movement of the cannula through the valve. This configuration leads to that the assembly may be delivered with the cannula already in position and ready for immediate use (e.g. connection to a fistula) where retraction of the needle is followed by instant and reliable closure of the valve. Once the valve is closed leakage of blood is prevented. In one embodiment, as a safety measure the automatic valve is designed so that re-insertion of the needle after it has been fully withdrawn is essentially prohibited.

According to one aspect of the invention said valve assembly comprises a valve seat, a sealing unit and a through passage. The sealing unit has a closing member and a biasing means, wherein the closing member is biased by the biasing means to sealingly abut the valve seat from outside the through passage thereby providing a closed position of the valve.

The biasing means is prebiased to sealingly press said closing member against the sealing surface of the seat with a predetermined pressure so that said closing member in a closed position tightly seals the through passage thereby closing the valve assembly.

In a preferred embodiment the closing member of the sealing unit is a plate-like member which in a sealed (closed) position is pressed onto the seat by said biasing means. When a needle is in position inside the assembly and extends there through, the needle body will keep the closing member in an open position, preventing it from snapping down to abut the seat. This means that a needle (cannula) which extends through the hub will cause the closing member to deflect leaving the contact with the seat thereby causing the valve assembly to keep an open position. In other words the body of the cannula will keep the closing member in a forced-open position exposing the aperture of the through passage. When the needle is removed, the closing member is released and will be forced by the biasing means to assume a closed configuration—i.e. snap down to a position abutting the seat and preferably also the periphery of the seat or the aperture of the through passage in a tight seal. In this position no blood or liquid may pass through the valve. The design of the valve provides the advantage that when delivered (i.e. before use) the cannula is allowed to extend through the catheter assembly and through the valve, while retraction of the cannula will lead to substantially immediate closure of the valve. The design of the assembly further leads to a very low friction between the cannula and the closing member, which enables for a smooth and easy retraction of the needle from the catheter and the valve assembly without any risk of sudden or irregular movements (which may otherwise risk damaging e.g. a fistula or the skin of a patient).

According to another aspect of the invention said valve seat is arranged on a seat body having an oblique front end comprising the frontal aperture/orifice of said through passage.

Said closing member preferably substantially matches the contour and shape of the oblique seat, meaning that in its neutral position the closing member is arranged to substantially abut the seat and cover the aperture of the through passage. Preferably however the closing member is prebiased to abut the seat with a predetermined pressure against the outer periphery around the orifice or around the orifice of the through passage. According to one embodiment, in a closed position the closing member aligns with the branch conduit and will in this configuration form an inner wall of the sealed conveying chamber. Hereby it will contribute to forming a smooth passageway between the inlet chamber and the distal conduit substantially void of any abrupt structural changes.

Preferably, when in a closed position the front side of the valve seat body will form an inner wall of the sealed conveying chamber, and said inner wall is in aligned configuration with the straight portion of the branch conduit. Preferably said straight portion of the branch conduit exhibits an angle α in relation to the rear end of the catheter between 90-180°, preferably between 110-175°, even more preferred between 135-170°. This leads to that the valve assembly in a closed position will contribute to enabling a careful transfer of blood through the catheter introducer assembly, and at the same time the oblique front seat will enable for achieving a tight fit between the flexing portion and the sealing surface around the orifice of said straight through passage.

According to another aspect of the invention said valve assembly comprises a rear coupling member which in a front portion provides a connection for said seat body and which in a rear portion comprises a coupling for a retaining member arranged to retain said cannula. In a preferred embodiment the rear coupling constitutes a coupling both for said retaining member and for a Luer-Lock™ coupling. Easy and quick decoupling of the retaining member, and thereby of the cannula, from the coupling member enables for a controlled release and withdrawal of the needle out of the catheter introducer assembly which is a significant advantage in order to attain a safe and smooth connection of the catheter to a fistula.

According to yet another aspect of the invention the coupling member is arranged with at least one collection compartment which in an assembled assembly is located at the rear side of the seat body. Hereby, in case a small blood volume would happen to pass the valve prior to that the sealing flap has assumed a closed position, such volume will be collected inside the compartment. In a closed configuration the valve will prevent any passage via the valve, and thereby the risk of any coagulated blood entering from the compartment into the passing blood stream is eliminated.

According to yet another aspect of the invention the biasing means of the sealing unit is made of a metal material, preferably stainless steel. Steel material has proven to be suitable for the purpose of achieving a spring-acting function, and the biasing means may, during manufacturing, be prebiased to assume a certain inherent shape (according to one embodiment of the invention a curved shape) and will also retain its inherent shape over time. It is to be understood that thanks to said prebiased biasing means the sealing unit and said closing member will be able to retake its inherent, original configuration after having been deflected.

According to yet another aspect of the invention the biasing means is made of a plastic polymer material or a polymer composite material, which provides the function of a spring.

According to yet another aspect of the invention the rear portion of the hub is provided with a pair of wings extending from the hub, which wings can be folded against one another to serve as a gripping member when the catheter shall be inserted/retracted into/out of the fistula and be brought to contact and to be attached releasably to the skin of the patient in order to fixate the catheter. In one aspect of the invention each of the wings comprises a groove arranged to match a branch conduit on the hub, and said wings are positioned onto the hub so that the wings, upon folding them against one another, will embrace said branch conduit so that said branch conduit will fit said grooves. This will contribute to a secure grip of the wings around the catheter introducer assembly. The gripping members will contribute to making the assembly very user-friendly and to that a stable and controlled insertion of a catheter into a fistula may even be performed using one hand only. In addition to the obvious advantage for the professional user (e.g. a nurse) this may lead to the possibility of home-treatment and that a patient can learn to connect him/herself e.g. to a dialysis equipment and not needing to go to a medical centre in order to get treatment.

According to yet another aspect each one of said pair of wings is provided with a perforation preferably positioned close to the hub, for enabling of tearing off the wings from the assembly if desired. This provides the advantage that the user may choose whether to handle the assembly by means of gripping the wings, or if he/she would rather exclude the wings they can easily be removed by tearing at the perforation. This also allows for adaption of the product once it is to be attached to the patient's skin: in case there is little space around the fistula one or both wings can be teared off for making room for the tubes and other equipment.

According to yet another aspect of the invention said wings are attached onto the hub via a sleeve, which is arranged to be rotatably mounted onto the hub. This means that when attaching the wings onto the patient's skin the hub of the catheter assembly may be rotated inside the sleeve either to the right or to the left in relation to the wings and the user (e.g. health care provider) may thereby choose a suitable position of the branch conduit (and the distal conduit) before attaching it onto the patient's skin. This provides the advantage that a user may choose the orientation of the distal conduit/tube, and hereby catheter assemblies for withdrawal and reintroducing blood respectively may be placed closer to each other on the patient's skin without the respective tubes of the dialysis apparatus getting entangled.

According to yet another aspect of the invention the exterior of the rear portion of the hub is provided with a roughened surface for providing a grip area when the catheter shall be inserted/retracted into/out of the fistula. The user is thus free to choose to grip the roughened surface rather than the wings when handling the catheter assembly.

BRIEF DESCRIPTION OF THE DRAWINGS

In the following detailed description, reference will be made to the accompanying drawings, in which:

FIG. 6B shows a seat body according to one embodiment, FIG. 6C shows the seat body of FIG. 6B provided with a sealing unit according to one embodiment of the invention.

DETAILED DESCRIPTION OF THE DRAWINGS

Figure 1:
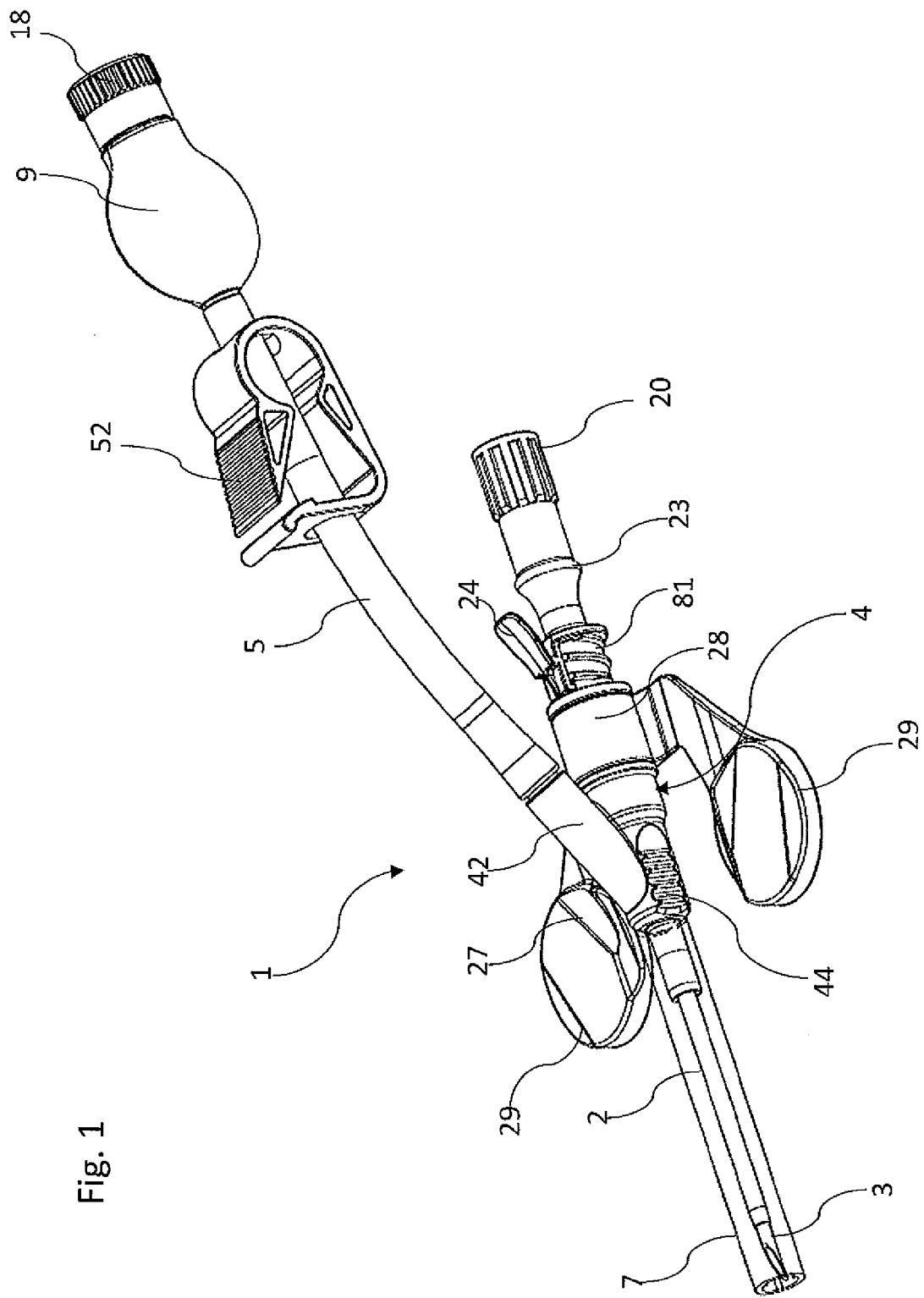
FIG. 1 is a perspective view of a catheter introducer assembly according to the invention.
Figure 2:
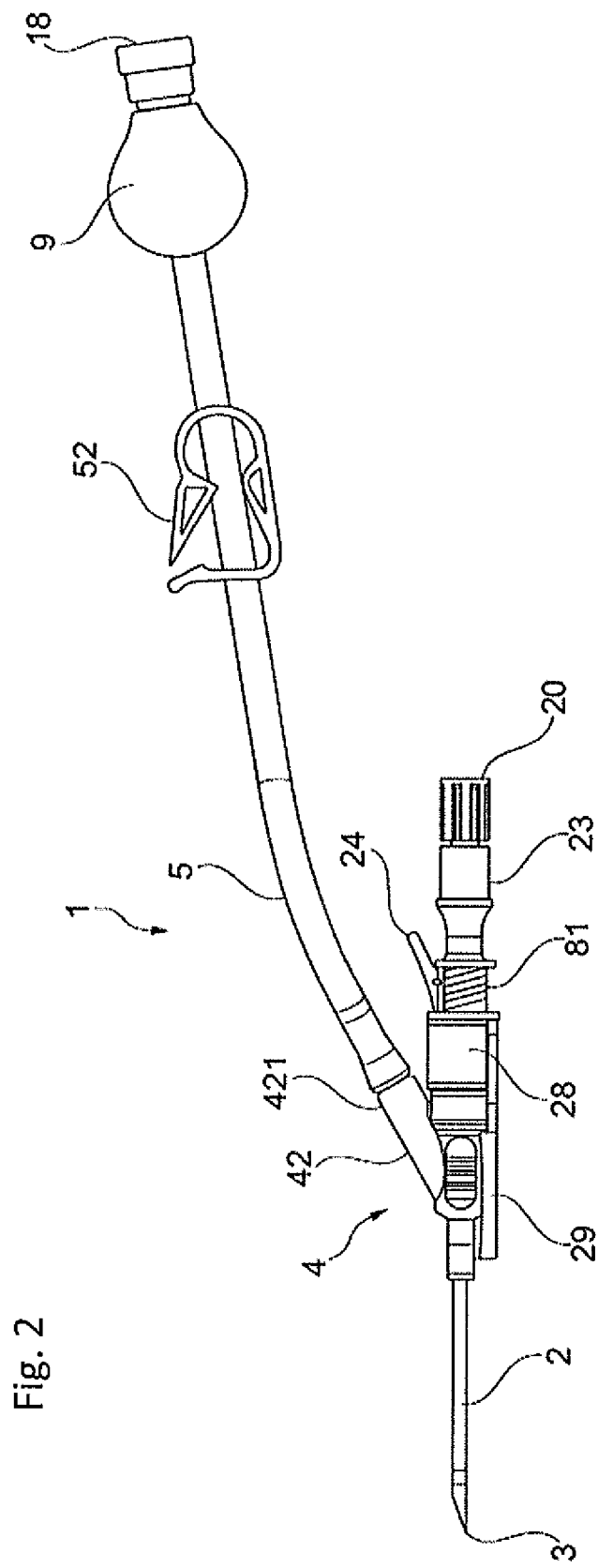
FIG. 2 shows the assembly in a view from a side.
Figure 3:
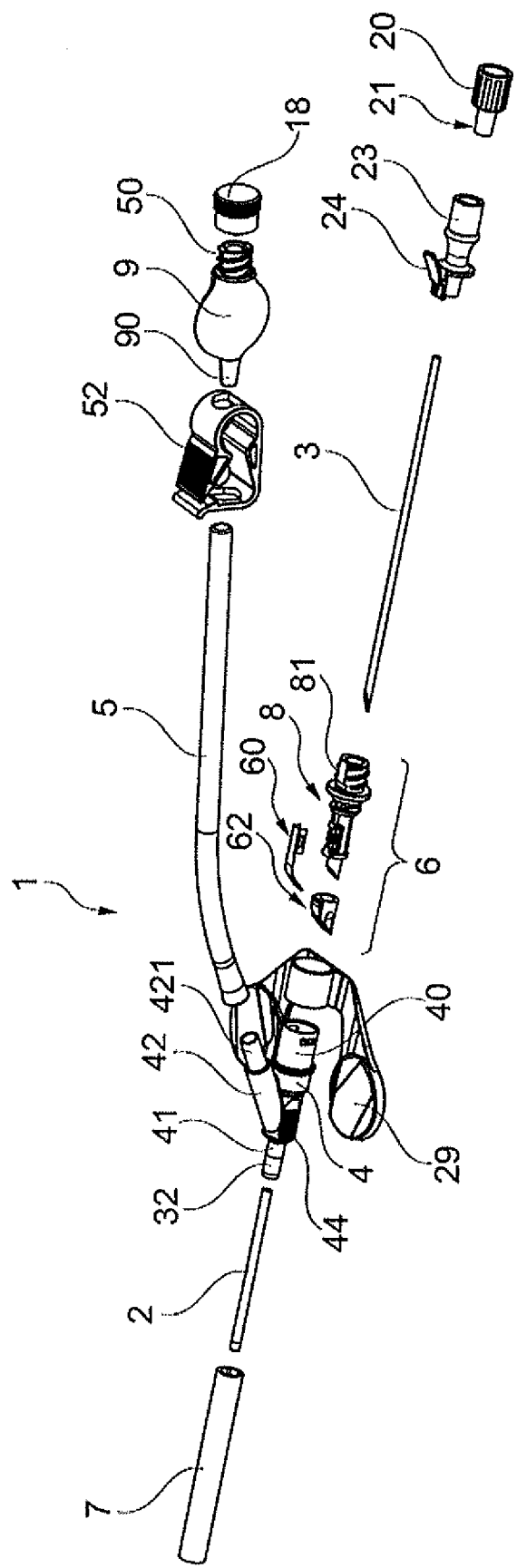
FIG. 3 is an exploded view, showing the parts of the assembly.
Figure 4A:
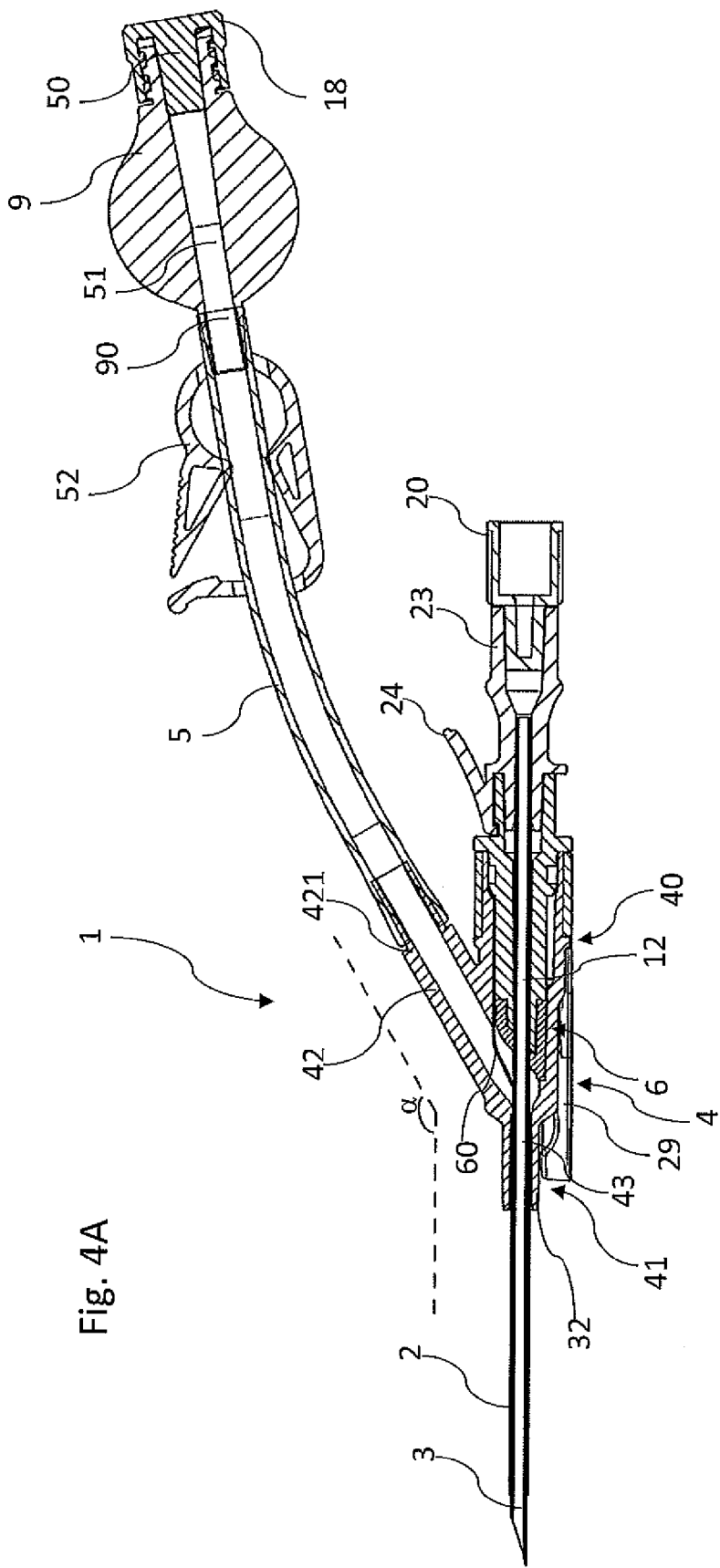
FIG. 4A shows the assembly in cross section.
Figure 4B:
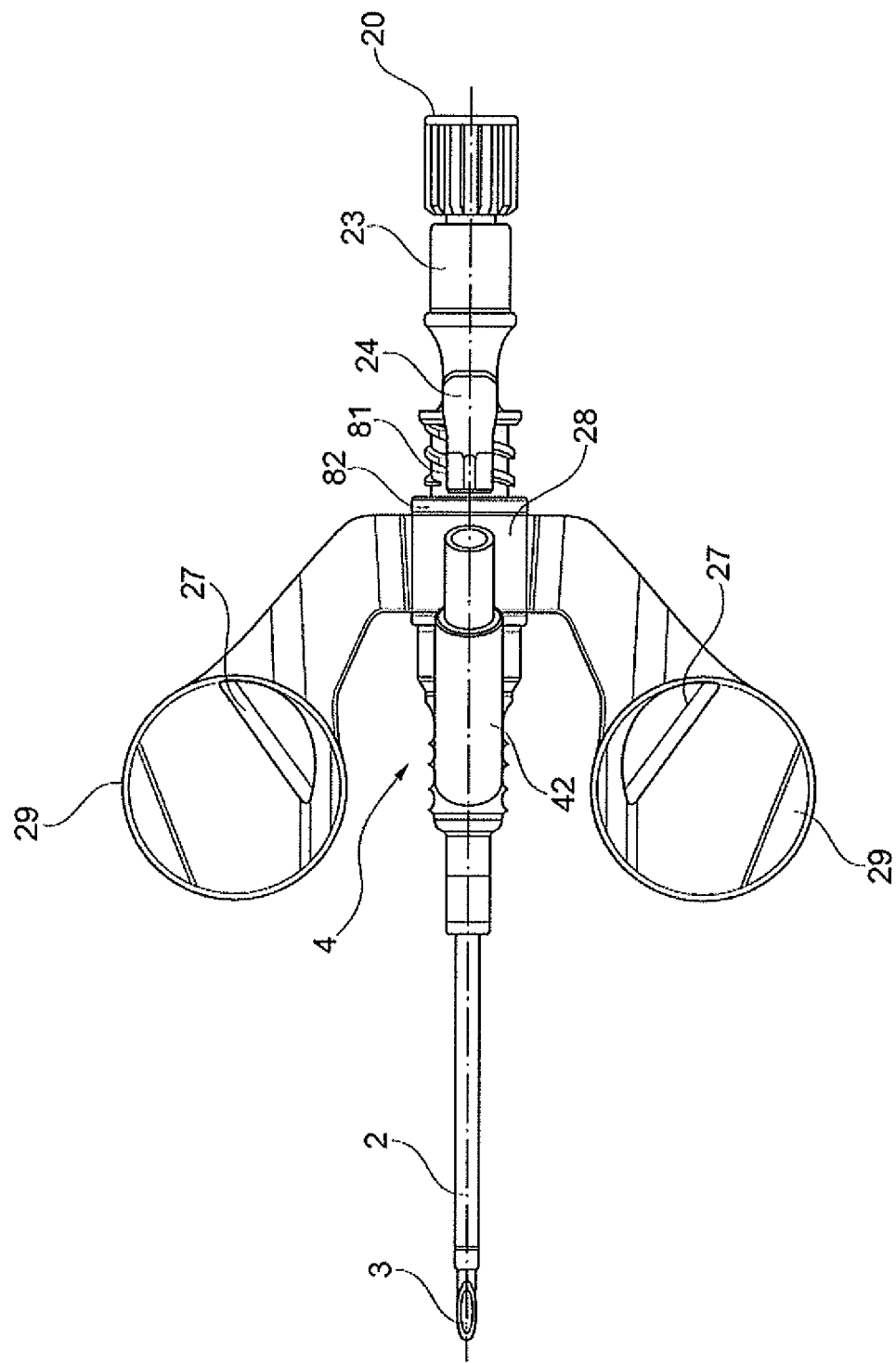
FIG. 4B shows the assembly from above.

The foregoing aspects and many of the attendant advantages of this invention will become more readily appreciated as the same become better understood by reference to the following detailed description, when taken in conjunction with the accompanying figures. Further, the description, and the examples contained therein, are provided for the purpose of describing and illustrating certain embodiments of the invention only and are not intended to limit the scope of the invention in any way.

In FIGS. 1-9a catheter introducer assembly is generally designated 1. FIGS. 1-7 show, in a schematic way, a first preferred embodiment according to the invention and FIG. 8A and FIG. 8B show a second and a third embodiment, respectively, according to the invention.

The drawings relate to an assembly 1 comprising a bifurcated connection piece (here referred to as hub 4) having a branch conduit 42 and a rear conduit 45 where the branch conduit 42 is connected between a catheter 2 and a distal conduit 5. This type of catheter introducing assembly 1 is suitable for conveying media into and out of a patient and may be used e.g. for dialysis by means of connecting the distal conduit 5 to a dialysis equipment. One of the advantages provided by the present invention is the efficient sealing provided by the inventive valve assembly 6 which is arranged inside the hub 4. As will be later explained more thoroughly the valve 6 is arranged with biasing means 68 which upon removal of the needle 3 from the hub 4 urges the valve 6 to assume a sealed configuration so as to prevent flow of medium out of the rear conduit 45.

Although the figures show a hub 4 comprising said branch conduit 42 it is to be understood that the valve assembly 6 is not limited to this type of assemblies. On the contrary, the valve assembly 6 according to the invention may be suitable for many types of medical devices (such as catheter introducing devices) serving the purpose of bringing media into and/or out of a body wherein a needle element 3 is used for establishing a conveying connection through a catheter, including hubs having branched or straight housings/hubs 4.

Although the invention is not limited thereto, hereinafter a type of catheter introducing assembly 1 will be described which is commonly used for blood dialysis, comprising two converging conduits 42, 45.

Referring first to FIGS. 1-5, the main parts of the catheter introducer assembly 1 comprise a catheter 2 (which according to the preferred embodiment is a conventional "catheter-over the needle" consisting of a thin plastic tubing), a cannula 3 in the form of a tubular needle (conventionally made of metal which extends through the catheter 2), a distal conduit 5 and a connection piece (here referred to as hub 4) connected to the catheter 2 and forming a connection between the catheter 2 and the distal conduit 5 for conveying blood or dialysis liquid to or from a patient.

The hub 4 has a frontal portion 41 and a rear portion 40. The rear portion 40 comprises two converging conduits 42, 45: one straight rear conduit 45 and one branch conduit 42. The rear conduit 45 comprises a narrow, straight passageway 12, herein also referred to as cannula passageway, extending from the rear end of the hub 4, through the rear portion 40 of the hub and mouths at the position of the branch conduit 42. The frontal nose portion 41 in front of the orifice of the branch conduit 42 is arranged with an inlet chamber 43 (inlet conduit 43) which forms an extension of the cannula passageway 12 and is coaxial with said cannula passageway 12. The inlet conduit 43 is arranged to receive and retain the distal (rear) end portion of a catheter tube 2 meaning that in an assembled state the distal end portion of the catheter tube 2 (i.e. the end portion which is retained by the inlet 43) is also coaxial with the straight passageway 12.

Said branch conduit 42 starts with a curve 420 and thereafter exhibits a straight portion 421 which extends to the distal conduit 5. The straight portion 421 of the branch conduit 42 extends obliquely rearwards relative to the straight cannula passageway 12 and inlet chamber 43 respectively. Preferably the straight portion 421 of the branch conduit 42 exhibits an angle $\alpha$ in relation to the inlet chamber 43 preferably between 90-180°, preferably between 110-175°, even more preferred between 135-170°. The inlet chamber 43, the curve 420 of the branch conduit 42 and the straight portion 421 of the branch conduit together establish a conveying connection between the catheter 2 and the distal conduit 5. When the valve assembly 6 is in a closed position said conveying connection forms a sealed conveying chamber 100 inside the main body of the hub 4 where the cross section of the sealed conveying chamber 100 preferably is void of any abrupt changes promoting an even flow path for passing blood or liquid between the catheter 2 and the distal conduit 5.

The hub 4 can be made of any suitable material, preferably a stiff plastic polymer material which can be sterilized. In one embodiment the hub is made of a still transparent plastic material. In another embodiment the hub 4 is made of a plastic material with an additive for providing a color to the hub 4.

The catheter 2 may be any conventional type suitable for the specific purpose, (e.g. conveying blood or dialysis liquid during dialysis treatment, intravenous liquid etc) however normally a catheter is made of a plastic polymer material such as polyurethane based plastic or fluorinated based plastic. Additives such as X-ray contrast components may optionally be added to the plastic material. The catheter may be a standard type or any other suitable type, such as e.g. tip-forming catheter tube comprising a conical rear end.

Figure 5:
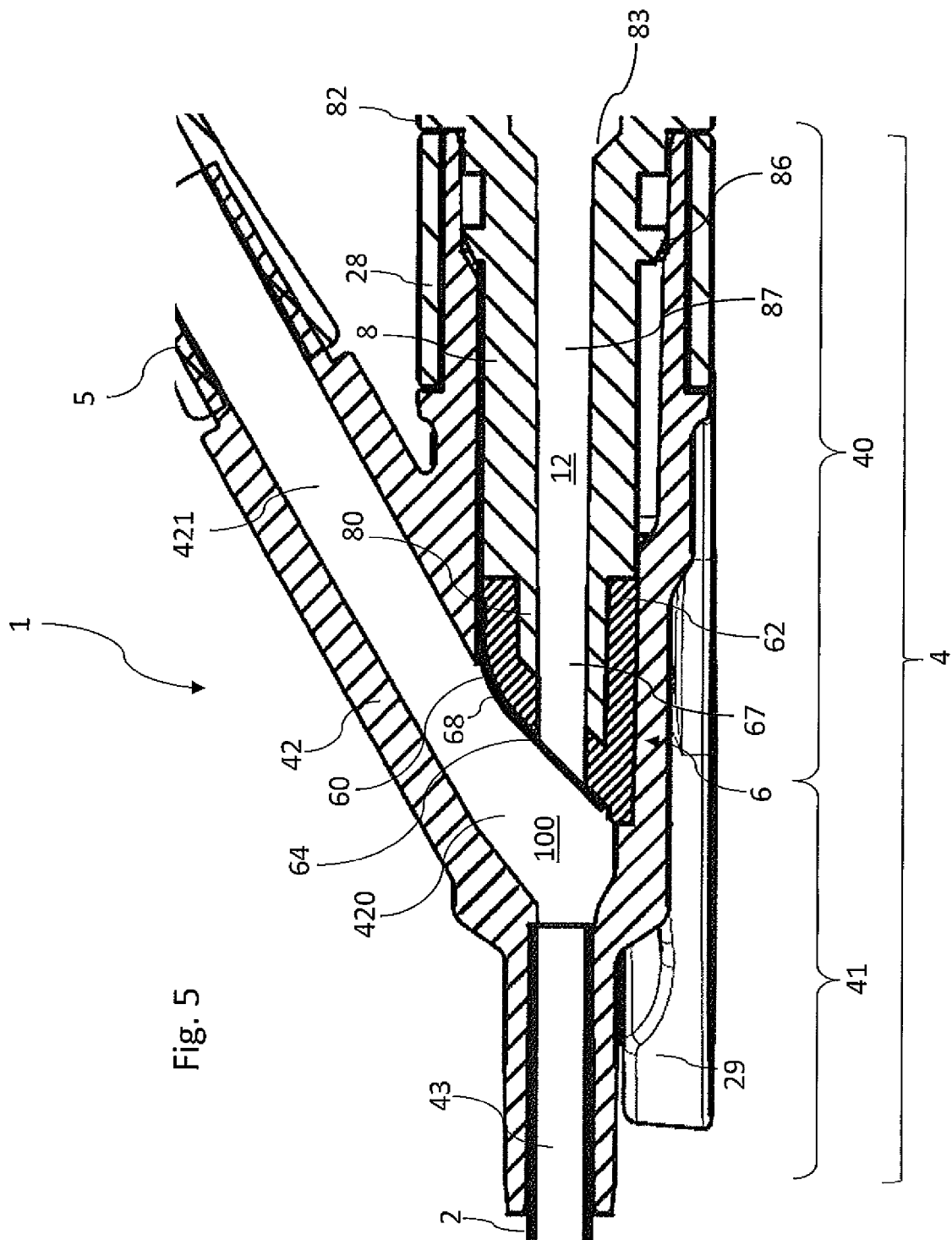
FIG. 5 shows a detail in FIG. 4A at a larger scale.

A valve assembly 6 according to the invention is fitted within the hub 4 (see e.g. FIG. 5). The valve assembly 6 has a through passage 67 and is positioned at the rear portion 40 of the hub 4, rearwise of and adjacent to the front of the branch conduit 42 such that the straight through passage 67 is aligned with the cannula passageway 12. One function of the valve assembly 6 is to prevent leakage of fluid (e.g. blood) through the rear conduit 45 (and the straight passageway 12) when the needle 3 has been removed from the assembly 1. For this purpose the valve 6 is arranged with biasing means 68 which urges a sealing unit 60 to assume a closed (sealed) configuration immediately upon removal of the needle 3. The valve assembly 6 will later be described in more detail.

A rear coupling member 8 is fitted inside the rear portion 40 of the hub 4, said coupling member 8 having a straight through bore 87. The coupling member 8 comprises a rear coupling portion 84 arranged to be releasably coupled to a retaining body 23 by means of an actuator 24, preferably in the form of a lever 24. In a preferred embodiment a groove 84 is arranged to form-fit with the lever actuator 24 of the retaining member 23, and a cannula 3 is attached to said retaining member 23, for instance by means of gluing or welding. At the rear part of the retaining member 23 there is attached a filter inside a filter adaptor 20. The rear portion 81 of the coupling member 8 is further provided with external threads forming a standard type threading for a Luer-Lock™ coupling 81 which function will later be described in more detail. Alternatively, the filter can be integrated into the filter adaptor 20 or the filter can be a separate component suitable to be fitted into the retaining member 23.

The retaining body 23 is arranged to retain the rear portion of said cannula 3, and is preferably irreversibly fixed to said cannula 3 e.g. by means of gluing or welding.

The cannula 3 according to the embodiment is of a type known per se, normally a metal needle with a sharp or blunt front end. When withdrawing the cannula 3 rearwise out of the hub 4 the retaining body 23 is first released by means of unlocking the lever 24 from the rear coupling 84 of the coupling member 8 and thereafter pulling the retaining body 23 in a rearwise direction thereby also withdrawing the cannula 3 out of the hub 4.

A filter adaptor 20 is connected onto the rear end of retaining member 23, for instance by a male coupling member 21 of the filter adaptor 20 being inserted into a substantially matching opening at the meeting end of the retaining member 23. The retaining member 23 includes a small chamber in a manner known per se in front of said filter adaptor 20, where a filter is positioned adjacent to the small chamber, said filter being permeable to air but not to liquid. The chamber forms a terminal for the lumen of the cannula 3 and the filter is provided in the front end of the filter adaptor 20 in a manner known per se.

A gripping and fixation member in the form of a pair of wings is designated 29, which will later be described in more detail. During transportation and storage, the frontal point of the cannula 3 and the catheter 2 are covered by a protecting cap 7, in a conventional way. The cap 7 is releasably pressed against the nose cone 32 at the frontal portion 41 of the hub 4.

The valve assembly 6 will now be described in more detail, referring mainly to FIG. 5 and FIGS. 6A-C. A preferred position of a valve 6 inside an assembled catheter introducer assembly 1 is shown e.g. in the enlarged view of FIG. 5 (wherein the valve 6 is seen in a closed position), and the main components of the valve 6 are shown e.g. in FIGS. 6A-C.

The valve assembly 6 comprises at least a sealing unit 60, a seat body 62 and a rear coupling member 8. In the exemplary embodiment shown herein the seat body 62 and the coupling member 8 are separate units, however it is equally possible to provide one integrated unit e.g. where the seat body 62 is pre-attached to the coupling member 8 and forms a front portion thereof. In a preferred embodiment said seat body 62 is made of a soft polymer material in order to provide for an efficient sealing surface for the sealing unit 60 as well as against the inner wall of the straight cannula passageway 12. Preferably, said coupling member 8 is made of a stiff material (either polymer or metal material) for providing a rigid and reliable support as well as a safe stopping 82 member at the back of the hub 4 once mounted thereto. Preferably said components of the valve assembly 6 are made material suitable for sterilization.

The seat body 62 comprises a through passage 67 and the coupling member comprises a straight bore 87. In assembled configuration the through passage 67 of the seat body 62 is coaxial with the through passage 87 of the coupling member 8. When the valve assembly 6 is fitted into a hub 4 the through passage 67 of the seat body 62 and the through passage 87 of the coupling member 8 are arranged to be aligned with the straight passageway 12 of the rear conduit 45.

Figure 6A:
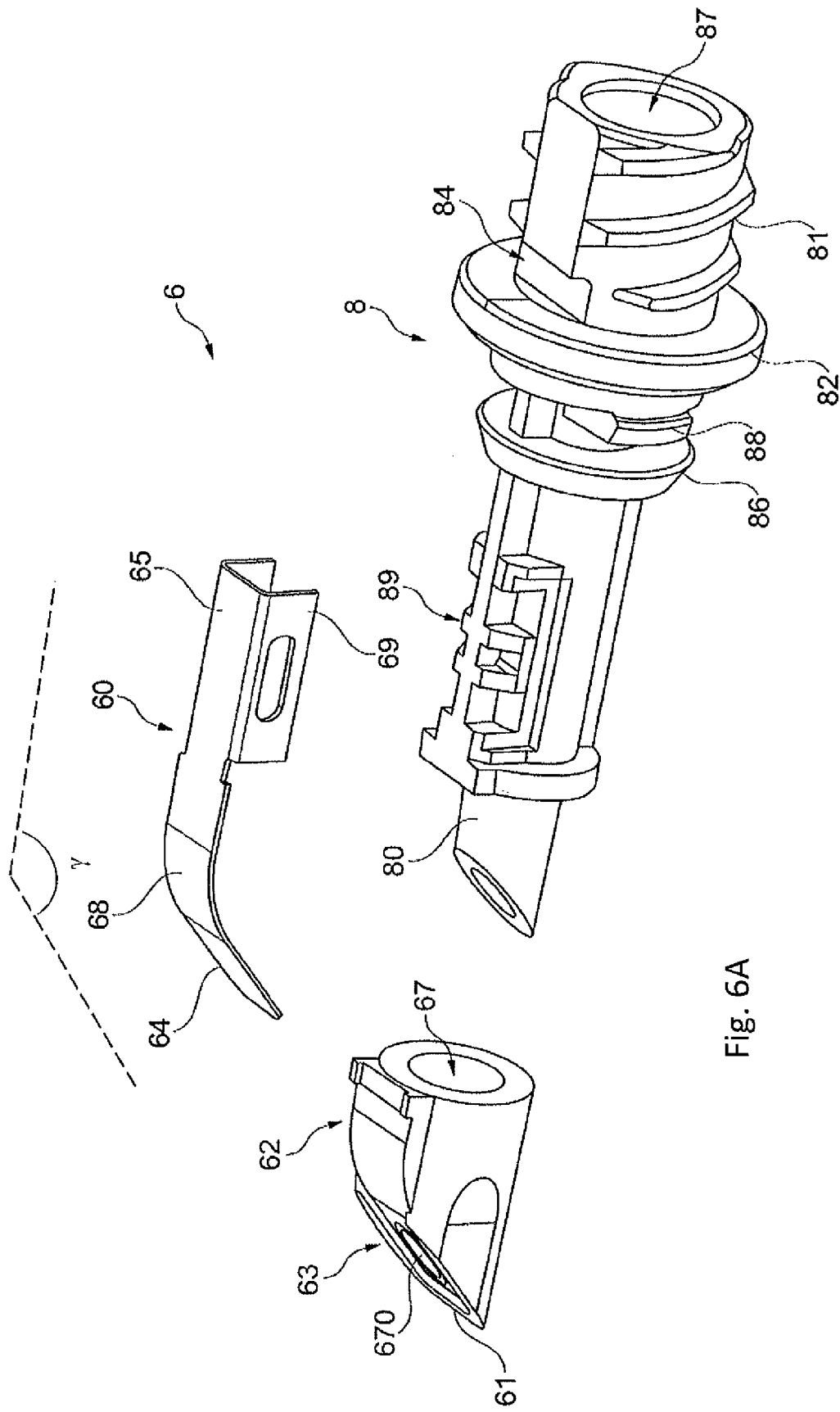
FIG. 6A shows an exploded view of a valve assembly according to one aspect of the invention.

Seat body 62 and coupling member 8 may be connected to each other by means of a male front portion 80 of the coupling member 8 being introduced into the through passage 67 of the seat body 62, which front portion 80 sealingly conforms to the diameter of the through passage 67. As seen in FIG. 6A the male portion 80 of the coupling member is designed with an oblique front matching the shape of an oblique seat 61 of the set body 62. When introducing the male portion 80 into the through passage 67 of the seat body 62 the matching oblique surfaces will safeguard rightful orientation of the coupling member 8 in relation to the seat body 62, which is advantageous during assembly of the valve components 60, 62, 8.

According to a preferred embodiment the sealing unit 60 comprises a fixed portion 65 arranged to be attached to the upper side of the coupling member 8 e.g. via a snap-in mechanism 69, 89, a middle biasing means 68 which is prebiased by means of having a curved design/shape, and a closing member 64 here in the form of a movable sealing plate 64. The biasing means 68 can be defined as a flexible portion 68 of the sealing unit 60. The different portions of the sealing unit 60 (the fixed portion 65, the closing member 64 and the biasing means 68) can be made of different materials or in the same material. In one embodiment the fixed portion 65, the biasing means 68 and the closing member 64 of the sealing unit 60 are formed in one piece, from the same material. In a preferred embodiment, however, at least the biasing means 68 (the curved portion of the closing member 60) is made of a resilient material, such as metal or polymer providing a spring function. Further, in a preferred embodiment the fixed portion 65, biasing means 68 and the closing member 64 form one integrated unit. The biasing means 68 creates a curved section on the sealing unit 60 and is arranged to provide a spring function and is preferably made of a resilient material, such as metal or polymer, for instance stainless steel, and may be deflected.

The valve 6 may assume an open and a closed position. Sealing unit 60 is shown in its forced open position in FIG. 7A and in its closed position in FIG. 7B. Said through passage 67 presents an aperture/orifice 670 on the seat 61, and said closing member 64 is biased by a biasing means 68 to sealingly abut the valve seat 61 from outside the through passage 67 so as to cover the aperture 670, thereby providing a closed position of the valve. Preferably the biasing means 68 is prebiased so that it, when the sealing unit 60 is in an unaffected/neutral state, will cause the closing member 64 to abut the seat body 62 so as to sealingly rest against and abut the sealing surface 63 provided around the orifice 670 of the through passage 67 with a predetermined pressure, assuming a closed position. Thus the closing member 64 serves as a sealing cover and can be moved between a closed and an open position.

The seat body 62 is shown from a front side in FIG. 6B. At its front end the seat body 62 exhibits a seat 61 arranged with a sealing surface 63 around a frontal aperture 670 of said through passage 67. When the valve 6 is in a closed position the biasing means 68 of the sealing unit 60 biases the closing member 64 to sealingly press against the sealing surface 63 with a predetermined pressure for tightly sealing the through passage 67.

In one embodiment the frontal portion of the seat body 62 is oblique so that an angle is formed between the oblique front seat 61 and the alignment of the through passage 67 extending through the seat body 62. In a preferred aspect the angle β is between 90-180°, preferably between 110-175°, even more preferred between 135-170°. The oblique front seat will enable for achieving a tight fit between the sealing flap 64 and the sealing surface 63 around the orifice of said straight through passage 67. Moreover the sealing unit 60 is designed so that, in a neutral position, an angle γ is formed also between the fixed portion 65 and the closing member 64. Preferably the angle γ is slightly smaller than the angle β. This will lead to that the closing member 64, when being biased by the biasing means 68 to abut the seat 61, will be pressed against the seat 61 and the sealing surface 63 with a predetermined pressure so that a tight and reliable seal is created inhibiting any fluid from passing through the valve 6.

In FIG. 6C there is shown, in a schematic way, a sealing unit 60 substantially matching the contour of the front end of the seat body 62 in a closed position. In a preferred embodiment the seat 61 exhibits a groove which is arranged to substantially match the shape and thickness of the closing member 64. Thus in a closed position the closing member 64 will be stably positioned within the groove at the seat 61 and also assume the correct position for creating a tight seal against the sealing surface 63. According to one embodiment the closing member 64 is provided with a protrusion on its under side—i.e. the side which is arranged to meet the seat 61. Preferably the protrusion substantially matches the dimensions/diameter of the mouth of the through passage 67. Thus when said valve 6 is in a closed position said protrusion will fit snugly into the through passage 67 thereby further improving the sealing function of the closing member 64.

The sealing surface 63 may for instance be made of a resilient material such as a suitable polymer, for improving the sealing fit between the seat and the closing member 64. It is understood that the herein referred to "sealed conveying chamber" 100 is defined by the portions of the main body of the hub 4 where through blood or dialysis liquid will be conveyed upon use of the assembly 1, i.e. said inlet chamber 43, curve 420 and branch conduit 42 respectively, and that said closing member 64 when the valve 6 is in a closed position will form an inner wall of the conveying chamber 100.

According to a preferred aspect of the invention the assembly 1 is delivered with a metal needle 3 extending through the cannula passageway 12 and the inlet port 43 of the hub 4, and also extending through the catheter 2 with its frontal end projecting a short distance in front of the front end of the catheter 2. In a configuration where the needle 3 is in place inside the catheter assembly 1, extending through the hub 4, the needle 3 also extends through the valve 6 in such a way that it keeps the closing member 64 in a forced open position, preventing it from snapping down to abut the seat 62. In this configuration the assembly 1 is ready for use, e.g. penetrating a fistula/skin of a patient. After penetration of the fistula the needle is 3 withdrawn rearwise out of the catheter 2, and subsequently out of the valve assembly 6. At the moment when the needle 3 is withdrawn rearwise out of the valve 6 the closing member 64 is released (since the needle body 3 which previously prevented the closing member 64 from moving is removed) and the biasing means 68 will cause the sealing unit 60 to instantly and automatically assume a closed, sealed position, where the closing member 64 tightly abuts the seat 61. Thus, in the closed position said rear conduit 45 and the straight passageway 12 are sealed from said conveying connection 43, 420, 421 and passage of blood or dialysis liquid through said valve assembly 6 is impeded. In other words, the conveying chamber 100 formed upon closure of the seal 6 is sealed from the rear portion 40 of the hub 4.

As has been described, a cannula extending through the catheter assembly 1 will force the sealing unit 60 to keep an open position. When retracting the cannula 3 rearwise, out of the hub 4, a frictional drag will arise between the edge 640 of the closing member 64 and the needle surface 3. In order to protect the needle surface from damage during this movement said closing member edge 640 is preferably arranged with a radius (i.e. comprising a rounded edge) so that no sharp edges will scrape the needle surface. Such configuration will also reduce the friction drag between the needle surface 3 and the closing member 64 leading to that the cannula 3 can be withdrawn in a smooth, continuous movement.

At the portion facing the conveying connection 43, 420, 421 the seat body 62 exhibits an oblique front end which, when the sealing unit 60 is in a closed position, aligns with the branch conduit 42 forming a smooth passageway 420 between the inlet chamber 43 and the straight portion 421 of the branch conduit 42, substantially void of any abrupt structural changes. This contributes to a careful conveying of the blood liquid which reduces the risk for hemolysis that could arise in case of turbulence in passing blood/liquid.

The assembly 1 preferably comprises a pair of wings 29. The wings are shown from a side e.g. in FIG. 2 and from a top view in FIG. 4B. In one embodiment of the invention each wing 29 comprises a groove 27 arranged to match the shape of the branch conduit 42 of the assembly 1. The wings 29 may provide two functions. Firstly, they can be used as gripping means when the cannula 3 together with the catheter 2 shall penetrate a fistula, something which is facilitated thanks to said grooves 27 since the branch conduit can be fixated within the grooves in the two wings 29 during gripping of the assembly 1. Secondly, they can be used for fixating the hub 4 and the catheter 2 to the body of the patient during the dialysis treatment, which normally has a duration of at least 4-5 hours why it is advantageous to be able to keep the catheter assembly components as still as possible during ongoing dialysis treatment.

Said pair of wings 29 are preferably connected to a cylindrical sleeve 28 projecting in a lateral direction from the bottom side of said sleeve 28, where said sleeve 28 is arranged to be mounted to snugly fit onto a rearwardly projecting cylindrical neck at the rear portion 40 of the hub 4. The preferred position of the wings, being at the rear side of the branch conduit 42, provides the advantage that the assembly 1 can be gripped in an ergonomic way and will achieve a beneficial center of gravity thus becoming user-friendly and easy to handle, easy to use when introducing a catheter 2 and uncomplicated to attach to the patient's skin. In a preferred embodiment the sleeve 28 is rotatably arranged onto the hub 4, meaning that a user may adjust the position of the hub 4 and the branch conduit 42 in relation to the wings 29 for instance after having introduced the catheter 2 into a patient and before fixating the assembly 1 on the patient's skin. The wings can be made in a plastic polymer material.

In the rear end of the distal conduit 5, there is preferably arranged a rear gripping member 9, here referred to as rear wing. The rear wing 9 consists of a comparatively flat object having a thin front male portion 90, which is pressed, glued or welded into the rear end of the distal conduit 5, and a rear male portion 50 with an external thread, which forms part of a Luer-Lock™ coupling including the lid 18. A passageway 51 extends through the rear wing 9. On the distal conduit 5, there is a clamp 52 of a type known per se. The edges of the rear wing 9 are preferably rounded. Due to the fact that the rear wing 9 is flat but nevertheless is void of any sharp edges, it is adapted to be employed as a gripping member as well as it can optionally be used as a fixing member for fixing also the rear part of the catheter introducer assembly 1 against the patient's skin. According to the embodiment, a piece of tape can be used for fixing the rear wing 9 against the skin, but also adhesive coatings on at least one of the two flat sides of the wing 9, covered by pieces of protecting foils, are conceivable.

An example of mounting together of a device 1 according to the invention is now to be described.

Said coupling member 8 and seat body 62 are fitted together. (Obviously, if they are one integrated unit this step is not necessary.) Next the cannula 3 is to be inserted through the through passages 87, 67 of the coupling member 8 and the seat body 62 respectively. This may be done in two ways. According to the first way the needle 3 is introduced with its rear end through the through passage 67 at the front of the seat body 62 and is further inserted through the through passage 67 of the seat body 62 and the bore 87 of the coupling member 8 until the rear end of the needle 3 projects out of the rear end of the coupling member 8. At this point the retaining member 23 is provided and attached to the needle 3 rear end after which said retaining member 23 is attached to the coupling member 8 by means of the coupling 24, 84. At the rear end of the retaining member 23 the filter adaptor 20 is attached. This way of introducing the needle 3 into the assembly 1 provides the advantage that the needle tip is untouched during the mounting and thereby does not run the risk of getting damaged. According to the second way of inserting the needle 3, the rear needle end is first coupled to the retaining member 23 and the filter adaptor 20. Thereafter the cannula front tip is inserted into the through passage 87, 67 via the rear inlet 83 at the rear side of the coupling member 8. This is simplified in that said rear inlet 83 exhibits a conical shape with a gradually decreasing diameter for guiding the cannula into the through passage 87, 67 without damaging the sharp needle tip. When the cannula is fully inserted the retaining member 23 is coupled to the coupling member 8 by means of the coupling 24, 84. Once the needle 3 is in place and extends through the coupling member 8 and the seat body 62 respectively said sealing unit 60 is attached onto the seat body 64 via said snap-in mechanism 69, 89. The closing member 64 will be forced by the presence of the cannula/needle 3 to assume an open position, with the flap edge 640 resting against the upper surface of the needle 3.

A connecting piece in the form of said hub 4 is provided with a catheter 2 fixated at its front end. Said hub 4 may be equipped with a gripping member in form of a pair of wings 29 attached onto the cylindrical rear end 40 of the hub 4 via a sleeve 28. The valve assembly 6 along with the cannula 3 is introduced via the rear portion 40 of the hub 4 into the straight passageway 12. When the seal 6 has reached the right position inside the hub 4, and the cannula 3 is extending properly though the catheter 2, a snap-in mechanism is actuated where protrusions 88 on the coupling member 8 will snap into matching slots 48 on the rear portion 40 of the hub 4 and fixes the seal 6 into the right position where said front end of the seat body 62 has a correct orientation with respect to the branch conduit 42. (The skilled person understands that many ways for fixating the seat 6 to the hub 4 are possible and that said snap-in mechanism is one of many possibilities.) When the valve assembly 6 is completely inserted into the hub 4a rear stopping flange 82 of the coupling member 8 is arranged to abut the rear end 40 of the hub 4. Said stopping flange 82 also has the function of locking said sleeve 28 of said pair of wings into place by means of abutting the sleeve 28 preventing it from getting displaced in an axial direction.

The seat body 62 is preferably arranged to sealingly conform to the shape/diameter of the straight passageway 12 so that a tight fit is created and a sealing relationship is achieved between the inner walls of the straight passageway 12 and the outer surface of the valve assembly 6. For further safeguarding a tight seal said coupling member 8 is preferably arranged with an annular gasket 86 around its waist, preferably made of a resilient material such as rubber, arranged to tightly press against the inner wall of the straight passageway 12.

Figures 7A, 7B:
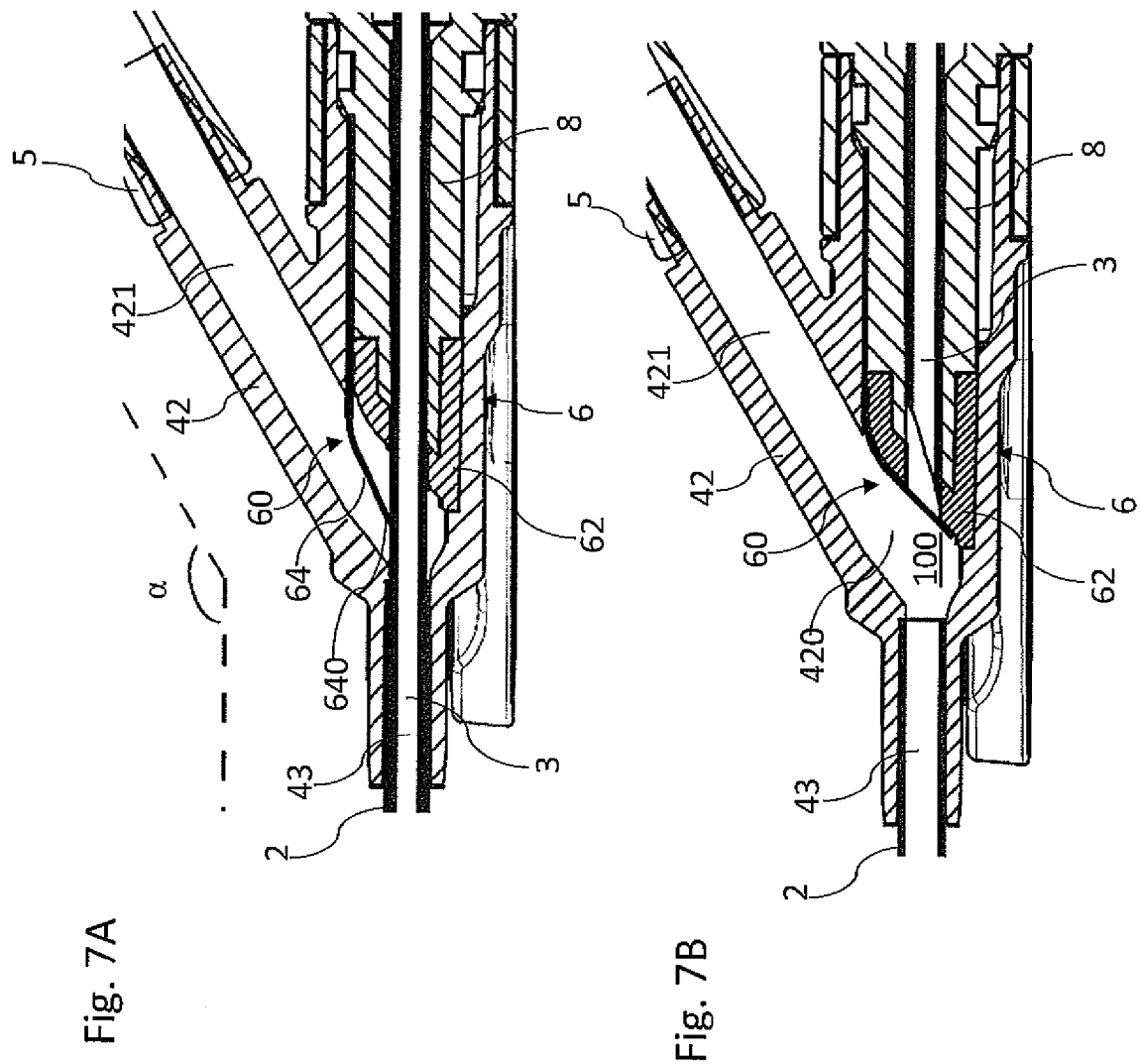
FIG. 7A and FIG. 7B show parts of the assembly in cross section at a larger scale before and after, respectively, a cannula, which is initially included in the assembly, has been removed.

As has previously been described the valve assembly 6 may assume a forced open and a prebiased closed position respectively. This is illustrated in the sequence of FIG. 7A and FIG. 7B, wherein FIG. 7A shows the assembly 1 before a cannula 3 has been removed, said valve 6 being in a forced open position, and FIG. 7B shows the assembly 1 after that the cannula 3 has been removed, said valve 6 having assumed a closed position.

The valve 6 is kept in an open position by the cannula 3 extending through the straight through passage 67, 87, while in a closed position the closing member 64 will prevent passage of blood or dialysis liquid through said straight through passage 87, 67. Furthermore, in a closed position the sealing unit 60 will form a wall of the conveying connection 43, 420, 421 inside the main body of the hub 4. When the valve 6 is closed the conveying connection 42, 420, 421 will form a sealed conveying chamber 100 inside the hub 4, where the cross sections are preferably void of abrupt changes promoting an even flow path for passing blood or liquid between the catheter 2 and the distal conduit 5. The sealing unit 60 is arranged to push with a certain pressure against the sealing surface 63 around the orifice of the through passage 67 in order to prevent rearwise leakage of blood. However said predetermined pressure/force is preferably not too strong since that could cause the sealing flap 64 to press too hard on the cannula 3 when the valve 6 is in an open position. Such too strong pressing force could lead to that the cannula 3 is pushed against the seat 62 leading to the upcome of an undesired friction drag when retracting the needle 3. This means the prebiased spring portion 68 is preferably arranged to fulfill the requirements of minimizing the friction drag between the needle and the seat 62/closing member 64 when the valve 6 is in an open position and at the same time creating a tight and secure seal when the valve 6 is in a closed position. Moreover, in a closed position the seal 6 is preferably arranged to resist overpressures as well as subpressures inside the conveying chamber 100—i.e. the closing member 64 should not accidentally open up even if a subpressure arises inside the conveying chamber 100 as might be the case during dialysis treatment.

A non-limiting example of use of a catheter introducer assembly 1 is now to be described, referring to FIGS. 1-9. The protective cap 7 is first removed. The user holds the assembly 1 with the wings 29 or optionally at the roughened portion 44 on the hub 4. In case the wings 29 are used they are brought against one another, in a finger grip, at the same time enclosing the branch conduit 42 within the grooves 27. By means of the fixation member, which is established by the wings 29, which are provided onto the rear portion 40 of the hub 4, the cannula 3 and the catheter 2 can be caused to penetrate the skin and fistula wall and be inserted into the fistula with small risk of undesired movements of the assembly 1, which could cause damage to the fistula. The front end of the needle 3 is used to penetrate the skin or the fistula of the patient, and the front end of the catheter 2 follows closely behind the needle 3 tip through the fistula/skin. As soon as the catheter 2 has been introduced into the fistula, the wings 29, which extend sideways from the bottom surface of the sleeve 28, may be fixed against the patient's skin by means of conventional adhesive tape or, if present, an adhesive on the wings 29. The hub 4 may thereafter be rotated in relation to the wings 29 to a desired position (e.g. to the right or left side) and fixed to the patient's skin. The high blood pressure inside the patient's blood circulation system will, immediately upon penetration by the needle 3, enter into the lumen of the needle and transfer there through until reaching the filter inside the filter adaptor 20 at the cannula terminal. Said filter is visible to the user, meaning blood can be detected as soon as it reaches the rear end of the needle since that will lead to that the filter is colored red. When blood has been detected in the assembly 1, the cannula 3 can be removed by means of withdrawal rearwards which is achieved by releasing and pulling the retaining member 23 out of the hub. Immediately upon withdrawal of the needle 3 from orifice 670 of the through passage 67 the biasing means (i.e. the spring portion 68) will cause the closing member 64 of the valve 6 to snap into a closed position, tightly abutting the seat 61 thus sealing the conveying chamber 100. No fluid may now pass rearwards out through the rear conduit 45.

As the needle 3 is retracted blood will enter into the catheter 2 and eventually also into the inlet port 43 and towards the branch conduit 42. Normally a user will be able to complete withdrawal of the needle 3 well in time before the interior of the hub 4 is filled with blood, and the valve 6 will close before any blood escapes out of the conveying chamber 100. If, however, any blood amount would enter through the through passage 67 it will be collected by a collection compartment inside the coupling member 8. Also, in this situation the valve 6 will prohibit any possibly coagulated blood from re-entering into the conveying chamber 100. After complete withdrawal of the cannula 3 the Luer-Lock™ closure 18 can be transferred from the rear end of the gripping member 9 to the rear end 81 of the coupling member 8 thereby completely sealing the assembly 1. Said rear male portion 50 (e.g. Luer-Lock™ coupling) of the distal conduit 5 is connected to the dialysis equipment and the user may then ease the clamp 52, so that blood is allowed to flow through the conveying chamber 100, via the branch conduit 42 and into the distal conduit 5, whereto a tube to/from the dialysis apparatus is be connected. As known by the skilled person the assembly 1 may be primed prior to use.

At such connection of an outlet (for withdrawal of blood from the patient) or inlet (for reintroducing blood into the patient) catheter 2 to the corresponding tubes of the dialysis apparatus, the rear wing 9 facilitates the opening of the Luer-Lock™ connection 18, as well as the connection of the tube via a Luer-Lock™ coupling 50 to the distal conduit 5, which also promotes a careful handling of the entire assembly 1 and hence a reduced risk that the catheter 2 would be disturbed or subjected to stresses which could damage the fistula. As has been mentioned above, the rear wing 9 can be used also for fixating the catheter introducer assembly 1, the distal conduit 5 and the hose against the skin of the patient by means of a piece of tape or adhesive coating on either side of the rear wing, whose rounded edges do not chafe or in any other way are inconvenient to the patient.

Figure 8A:
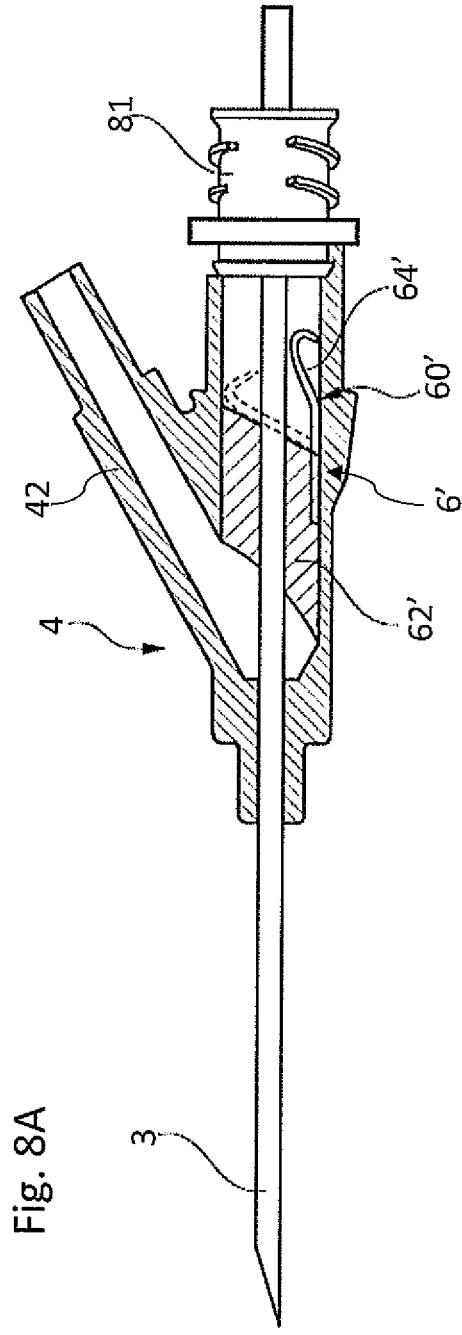
FIG. 8A illustrates a valve assembly according to a second embodiment of the invention.

In FIG. 8A there is illustrated, in a schematic way a second embodiment of the valve assembly 6' according to the invention, here with the sealing unit 60' having a reversed position compared to in the valve 6 seen in FIGS. 1-7. The seat body 62' exhibits an oblique front end aligned with the branch conduit 42 of the hub 4, and at its rear portion there is arranged the sealing unit 60'. The sealing unit 60' comprises a fixed portion 65', a biasing means 68' and a closing member 64' wherein said closing member here is in the form of a sealing plate 64'. The sealing unit 60' may assume a forced open and a closed position, wherein said biasing means preferably is prebiased to sealingly press said closing member 64' against the sealing surface around the through passage orifice at the rear side of seat 62'. In FIG. 8A there is shown an assembly 1 with a needle 3 extending from the rear to the front, and at the same time the sealing unit 60' is shown in both its open and in its closed position in the same figure wherein the sealing unit 60 in the closed position is drawn in dashed lines. It is to be understood that this outline is merely for the purpose of illustrating the function of the valve assembly 6': in reality said needle 3 is to be removed from the valve in order for the closing member 64' to assume a closed position.

Figure 9A:
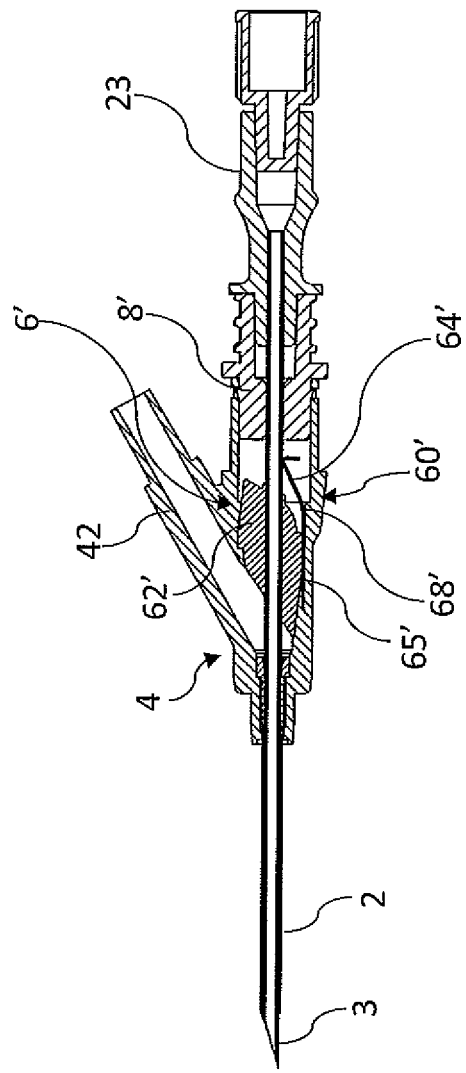
FIGS. 9A-B illustrate in sequence the closing of a valve assembly according to a second embodiment of the invention.
Figure 9B:
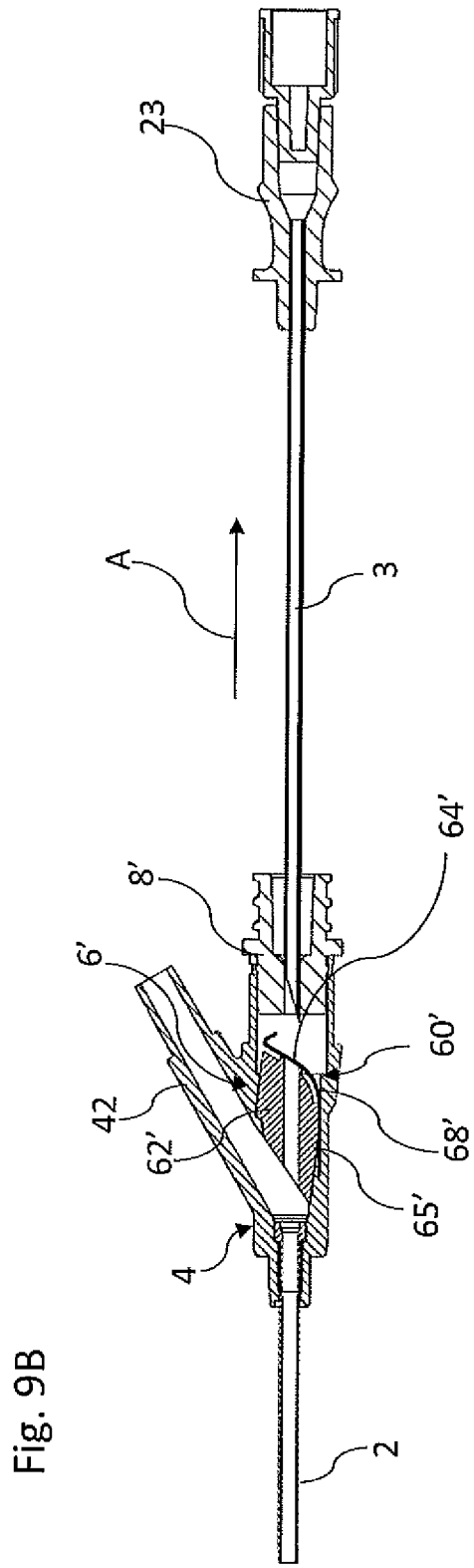

For better understanding of the function of the valve assembly 6' according to the second embodiment reference is made to FIG. 9A-B wherein is shown in sequence the withdrawal of a needle 3 (where the withdrawing motion is illustrated with an arrow A) and subsequent automatic closure of the valve 6' by means of the sealing unit 60' assuming a closed position as in FIG. 9B.

Figure 8B:
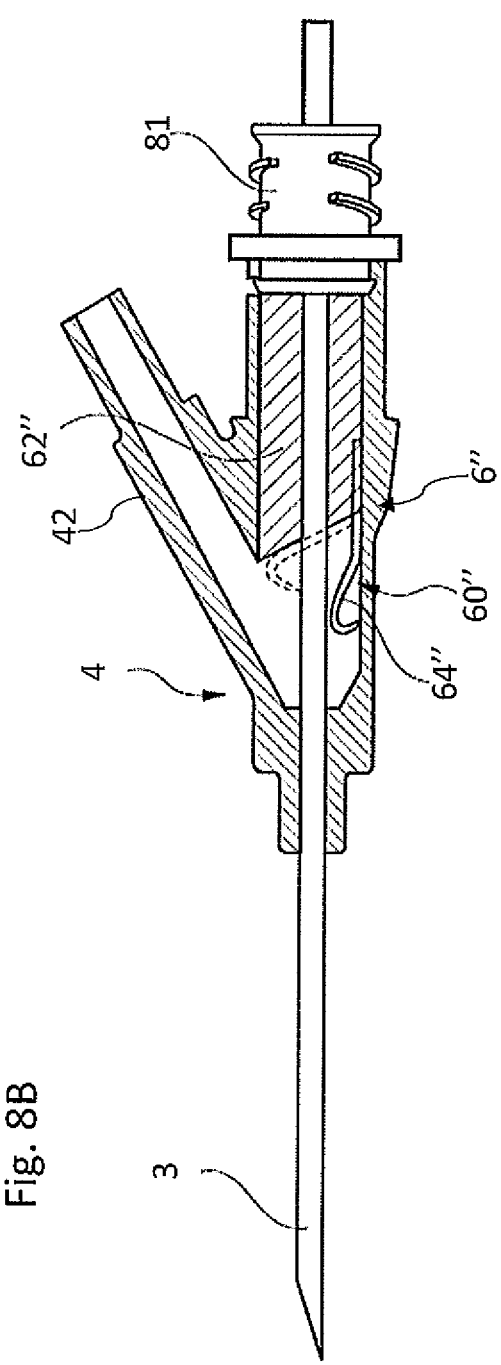
FIG. 8B illustrates a valve assembly according to a third embodiment of the invention.

In FIG. 8B there is illustrated, in a schematic way, a third embodiment of the valve assembly 6" according to the invention, here with the sealing unit 60" being positioned upside down compared to in the valve 6 seen in FIGS. 1-7. This third valve embodiment comprises the corresponding features as disclosed in connection to the preferred first embodiment of the invention, the only difference being that the sealing unit 60" at the front of the seat body 62 is arranged to be positioned underneath the cannula 3 rather than above it.

There is thus provided a catheter introducer assembly 1 comprising a catheter 2, a cannula 3 extending within said catheter 2, a proximal conduit 5, a hub 4 connected to the catheter 2 and forming a connection between the catheter and the proximal conduit 5 for conveying blood, dialysis liquid or other liquid to or from a patient, and a branch conduit 42 connected between said catheter 2 and said proximal conduit 5, said hub 4 comprising a rear portion 40 through which extends a straight passageway 12 which is coaxial with an end portion of the catheter 2, and a frontal portion 41 at the mouth/orifice of said branch conduit 42 said catheter being connected to the frontal portion 41, wherein said cannula 3, preferably in the form of a tubular metal needle, is arranged to be removed out of the hub 4 to establish a conveying connection 43, 420, 421 between the catheter 2 and the proximate conduit 5, wherein said hub 4 further comprises a valve assembly 6 which has a sealing member 60 with a preferably prebiased sealing flap 64 and which is arranged to assume an open position and a closed position, wherein in said open position the cannula 3 is arranged to extend through said valve, and wherein in said closed position passage of blood or dialysis liquid through said valve 6 is prevented and said sealing member 60 in a closed position is arranged to seal said straight passageway 12 from said conveying connection 43, 420, 421.

The invention is not to be seen as limited by the preferred embodiments described above, but can be varied within the scope of the appended claims. For instance, said closing member 64 may have various shapes as long as it covers said through passage 67. It is also possible to arrange the sealing valve 6 in various orientations, as is also understood from the previously described second and third embodiments of the valve 6. In other words, the sealing unit 60 can assume an orientation as the one seen in FIGS. 1-9, where the flap 64 is arranged to move between an open and a closed position essentially in a vertical plane, or it may be modified to assume any other outline without departing from the scope of the invention.

Also, it is conceivable to integrate a seat 61 and possibly a sealing surface 63 with the hub 4, meaning that the interior of the rear conduit 45 would be arranged with some kind of interior structure providing the same sealing function as the herein described seat body 62. In such an embodiment the sealing unit 60 would be arranged to, in a closed position, seal against a structure which is an integrated part of the hub 4.

Furthermore the skilled person understands that the assembly as the one herein described may be used for introducing a catheter into a patient for other treatments aside of dialysis, for instance intravenous therapy or other medical treatments. Also, the valve 6 can be mounted into any type of hub 4 where sealing following removal of a needle 3 from the hub 4 is desired.

The invention claimed is:

1. A catheter introducer assembly comprising:
   a catheter;
   a cannula extendable within said catheter; and
   a hub connected to the catheter for conveying blood, dialysis liquid or other liquid to or from a patient, said hub comprising a rear conduit through which there extends a straight passageway, which is coaxial with an distal end portion of the catheter, and a frontal portion, said catheter being connected to the frontal portion, wherein said cannula, is arranged to be removed out of the hub to establish a conveying connection between the catheter and the hub, wherein said hub further comprises a valve assembly being positioned at a rear portion of the hub rearwise of and adjacent to the conveying connection, said valve being arranged to assume an open position and a closed position, wherein in said open position the cannula is arranged to extend through said valve, and wherein in said closed position said sealing unit is arranged to seal said rear portion from the conveying connection so as to prevent passage of fluid from said conveying connection into the rear conduit, wherein the valve assembly comprising:
   a valve seat with a through passage, said through passage presenting an aperture on the seat; and
   a sealing unit comprising a movable closing member biased by a biasing means to sealingly abut the valve seat from outside the through passage so as to cover the aperture thereby providing a closed position of the valve, wherein a portion of a seat member that is arranged to face the closing member is an oblique surface having an angle ($\beta$) in relation to the through passage is between 110-175°, said assembly further comprising a branch conduit connected between said catheter and a distal conduit so that the said hub forms a connection between the catheter and the distal conduit for conveying blood, dialysis liquid or other liquid to or from a patient via the distal conduit, wherein the portion of said seat member which faces the conveying connection has an oblique front end which when the sealing unit is in a closed position aligns with the branch conduit forming a smooth passageway between the inlet chamber and the branch conduit substantially void of any abrupt structural changes to promote an even flow path for passing blood or liquid between the catheter and the distal conduit to reduce a risk of turbulence during transfer of the blood or liquid, and the reduced risk of turbulence reduces a risk of hemolysis when transferring blood.

2. The catheter introducer assembly according to claim 1, wherein said valve assembly comprises a straight through passage arranged to be coaxial with said straight passageway, wherein the valve assembly in said open position will allow for said cannula to extend through said straight through passage, and wherein the valve assembly in said closed position will prevent passage of blood or dialysis liquid through said straight through passage.

3. The catheter introducer assembly according to claim 1, wherein said valve assembly comprises a coupling member which in a front portion forms a connection for said seat and which in a rear portion comprises a coupling for a retaining member arranged to retain the rear portion of said cannula.

4. The catheter introducer assembly according to claim 1, wherein the rear portion of the hub is provided with a pair of wings and said wings are attached onto the hub via a sleeve, which sleeve is arranged to be rotatably mounted onto the hub.

5. The catheter introducer assembly according to claim 1, wherein the exterior of the rear portion of the hub is provided with a roughened surface for providing a grip area when the catheter shall be inserted/retracted into/out of the fistula.

* * * * *